United States Patent [19]

Dallal et al.

[11] Patent Number: 4,658,839

[45] Date of Patent: Apr. 21, 1987

[54] HAIR CONDITIONING AND ENHANCING APPLICATOR WRAP, COMPOSITION AND METHOD

[75] Inventors: Joseph A. Dallal, Bridgeport; Arnold Rubinstein, Norwalk, both of Conn.

[73] Assignee: Zotos International Inc., Stamford, Conn.

[21] Appl. No.: 784,343

[22] Filed: Oct. 4, 1985

[51] Int. Cl.[4] .............................................. A45D 7/00
[52] U.S. Cl. .......................................... 132/7; 424/70
[58] Field of Search ................................ 132/7; 424/70

[56] References Cited

U.S. PATENT DOCUMENTS

| | | | |
|---|---|---|---|
| 4,331,167 | 5/1982 | Wajaroff | 132/7 |
| 4,397,322 | 8/1983 | Arbaczawski | 132/7 |
| 4,438,095 | 3/1984 | Grollier | 132/7 |
| 4,445,521 | 5/1984 | Grollier | 132/7 |

*Primary Examiner*—Gregory E. McNeill
*Attorney, Agent, or Firm*—Mattern, Ware, Stoltz & Fressola

[57] ABSTRACT

By providing a flexible, easily applied carrier which incorporates a combination of cationic hair conditioning agents and a water soluble or emulsifiable silicone-based compound, a unique hair treatment system is achieved. Preferably, the flexible carrier or applicator is constructed for being wrapped either entirely or partially about a head of hair and also incorporates hair enhancing agents, such as plant and herb extracts and, if desired, coloring agents, to further condition and enhance the hair. In the preferred embodiment, the hair treatment applicator is wrapped about the entire head of hair after shampooing, with the hair conditioners and hair enhancing agent contained therein being transferred to all of the hair fibers by the application of a hot towel to the wrapped applicator and subsequent thorough rubbing.

16 Claims, No Drawings

HAIR CONDITIONING AND ENHANCING APPLICATOR WRAP, COMPOSITION AND METHOD

TECHNICAL FIELD

This invention relates to hair conditioners and enhancers and more particularly to hair treatment systems employing flexible applicators or wraps, and their methods of use.

BACKGROUND ART

Human hair requires cleaning, since the hair fibers become soiled, both from environmental contamination as well as contamination and soiling from chemical agents produced by the body. Generally, shampooing is employed to clean the hair by removing excess soil and body oils which have built up on the hair fibers. Unfortunately, while being capable of cleaning the hair fibers, shampoos generally leave the hair stripped, over-processed and difficult to manage.

In an attempt to eliminate these problems, various hair conditioning aids have been developed. In fact, hair conditioning aids are numerous and have appeared in almost every conceivable form—liquids, solids, emulsions, aqueous and oil solutions as well as chemicals embedded in flexible substrates which are rubbed throughout the hair to achieve transfer to the hair. Unfortunately, these prior art systems have been unable to attain all of the requirements for a good hair conditioner.

In general, a hair conditioner should be capable of effectively grooming the hair and keeping it in place, thereby leaving the hair natural in appearance, without any evidence that a hair conditioner has been used. Clearly, no oily film should remain on the hair fibers which can act as a dirt catcher. Furthermore, the hair conditioner must leave the hair with a high luster, gloss, sheen, as well as provide the entire head of hair with a full-bodied appearance, with the hair being easily managed and feeling soft and silky.

In addition to being unable to provide all of these qualities, prior art hair conditioners are also typically difficult to thoroughly apply to all of the hair fibers. Furthermore, many prior art compositions are cumbersome to use.

Therefore, it is a principal object of the present invention to provide a hair conditioning and enhancing applicator-wrap which is easy to employ and effectively imparts all of the desirable qualities to the hair fibers.

Another object of the present invention is to provide a hair conditioning and enhancing applicator-wrap having the characteristic features described above which is simultaneously applied throughout the entire head of hair in a single operation.

Another object of the present invention is to provide a method for employing the hair conditioning and enhancing applicator-wrap, having the characteristic features described above, which is easy to follow and provides the desired conditioning and enhancement of each and every hair fiber.

Other and more specific objects will in part be obvious and will in part appear hereinafter.

DETAILED DESCRIPTION OF THE INVENTION

The present invention eliminates the prior art difficulties by providing a hair conditioning and enhancing applicator-wrap which incorporates both a cationic hair conditioning agent and a water soluble or emulsifiable silicone-based compound. Preferably, these hair conditioning agents are saturated into the applicator-wrap and then dried, to provide a highly concentrated, effective composition. The applicator-wrap preferably comprises a size and shape which allows application of the retained composition to the entire head of hair easily and conveniently.

In the preferred embodiment, the applicator-wrap or carrier comprises woven or non-woven fibrous material within which the hair conditioning composition is completely absorbed, substantially throughout the fibrous material. In this way, application throughout the entire head of hair is attained simultaneously, and thorough, complete hair conditioning is realized.

In order to impart luster, sheen, gloss, manageability and sensual appeal, the hair treatment applicator-wrap also preferably incorporates hair enhancing agents, such as plant extracts, herb extracts, fragrance enhancers and other hair enhancing emollients. All of these compounds are contained in the applicator-wrap in the relative proportions which have been found to produce the most desirable results.

Construction of Applicator Substrate

It is believed that any woven or non-woven fibrous substrate can be employed as the carrier or applicator-wrap for the hair conditioning and enhancing composition, provided the minimum required quantity of the composition can be retained therein. In addition, the fibrous substrate can be made from either natural fibers or synthetic fibers.

In selecting a suitable fibrous substrate for use as the applicator-wrap of the present invention, a major consideration is the absorptive quality of the fibrous material, as well as its flexibility and ease of handling. As is fully detailed below, a substantial concentration of the hair conditioning agent is required in order to attain the desired results. Consequently, the fibrous substrate must be capable of absorbing and holding the desired conditioning agents for subsequent transferral to the hair.

The preferred substrate comprises either woven or non-woven fibrous materials selected from the group consisting of rayon, nylon, polypropylene, and polyester. In addition, blends of these fibrous materials has been found equally efficacious, such as a rayon and polypropylene blend.

Furthermore, the overall size of the applicator wrap of the present invention can be widely varied, depending upon the particular use desired. As is more fully detailed below, the applicator-wrap of the present invention incorporates a highly concentrated hair conditioning and enhancing composition.

Although the resulting hair conditioning and enhancing applicator-wrap of the present invention is preferably employed as a full head system which is applied to all of the hair fibers of the head, the hair conditioning and enhancing applicator-wrap of the present invention can be employed selectively on bleached or severely damaged hair fibers, in order to impart the desired conditioning and enhancing effects to specific, limited areas of the hair. Consequently, the overall size and shape of the applicator-wrap of the present invention can vary from about two inches by three inches to about sixteen inches by thirty-eight inches.

In order to provide the preferred full head application, the preferred size for the applicator-wrap of the present invention is thirteen inches by twenty-four inches. With an applicator-wrap having these preferred dimensions, most heads of hair can be quickly and easily entirely wrapped, with the applicator being held in place with a single clip.

In addition to the desired length and width, the preferred fibrous carrier within which the hair conditioning and enhancing composition is retained is preferably about 0.016 inches and 0.017 inches thick. It has been found that by providing a fibrous substrate with this thickness, the desired concentration of the hair conditioning and enhancing composition can be easily retained and an extremely effective hair conditioning applicator-wrap is attained.

If desired, the thickness of the applicator-wrap of the present invention can be varied, depending upon the formulation of the hair treatment composition or the particular limitations or specific uses to which the applicator-wrap is to be employed. Generally, an effective applicator-wrap may comprise a thickness of between about 0.001 inches and 0.050 inches.

Hair Conditioning Composition

In order to impart the desired gloss, sheen and luster to the hair, as well as improve the manageability and luxurious, full-bodied appearance, a unique hair conditioning and enhancing composition has been developed. The primary constituents of the hair conditioning and enhancing composition of the present invention comprise a cationic hair conditioning agent and a water soluble or emulsifiable silicone-based compound.

For purposes of clarity and explanation, the constituents incorporated into the hair treatment composition of the present invention are detailed using the designations adopted by the Cosmetic, Toiletry and Fragrance Association (CTFA), and detailed in the CTFA Cosmetic Ingredient Dictionary, 3rd Edition, Published 1982. In addition, where available, the CTFA designations are supplemented with the chemical names and/or formulas.

The preferred cationic hair conditioning agent comprises quaternium-18, or a quaternary ammonium salt, the use of which is well known and fully disclosed in the prior art. The preferred quaternary ammonium salt employed in the present invention comprises dimethyl dihydrogenated tallow ammonium chloride. However, most other well-known, commonly employed quaternary ammonium salts, or equivalents, can be used in the present invention with substantially equal efficacy, without departing from the present scope of the invention. Quaternium-18 or quaternary ammonium salt has the following general formula:

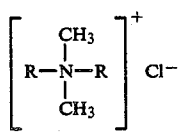

where R=hydrogenated tallow fatty radicals.

As discussed above, in addition to the quaternium-18 or the quaternary ammonium salt, the hair conditioning composition of the present invention also incorporates a water soluble or emulsifiable silicone-based compound. In the preferred embodiment, dimethicone copolyol or dimethylsiloxane-glycol copolymer comprises the silicone-based compound. The preferred dimethicone copolyol is nonionic and water soluble, and comprises a polymer of dimethylsiloxane with polyoxyethylene and/or polyoxypropylene side chains. The following represents the general formula for dimethicone copolyol:

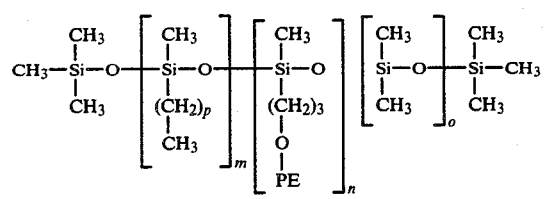

where $PE = (C_2H_4O-)_x(C_3H_6O-)_yH$.

The incorporation of a silicone-based compound provides the hair with added luster and sheen, as well as imparting added lubricity to the hair for increased slip and an increased silky feeling. Furthermore, the silicone-based compound provides a synergistic effect, increasing the action of the other constituents used in the hair treatment composition.

Although the use of dimethicone copolyol is preferred, other water soluble or emulsifiable silicone-based compounds can be employed, without departing from the scope of the present invention. One other alternate compound is dimethicone, which is a mixture of fully methylated linear siloxane polymers end blocked with trimethylsiloxy units. Empirically, the formula for dimethicone is $(C_2H_6OSi)_xC_4H_{12}Si$, with the following being representative of its general formula:

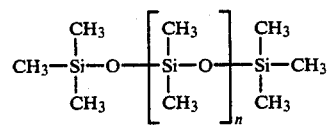

In addition, amodimethicone can be employed as the silicone-based compound. Amodimethicone is a silicone polymer end blocked with amino functional groups. Its formula is represented as follows:

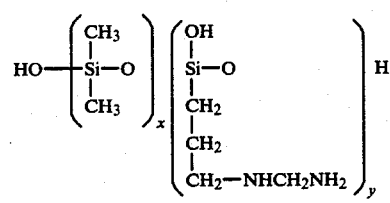

where x has a value of 4 or more.

Another silicone compound which can be employed is stearoxytrimethylsilane which is an organo-silicon compound having the empirical formula of $C_{21}H_{46}OSi$. Its formula generally conforms to the following:

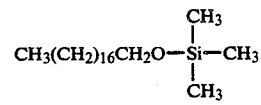

In addition, stearoxy dimethicone can be employed, which is a polymer of dimethylpolysiloxane end blocked with stearoxy groups.

Furthermore, the silicone compound employed in formulating the hair treatment composition employed in the applicator-wrap of the present invention can be a quaterized silicone compound or a betaine silicone compound. A typical quaternized silicone compound is polysiloxane polydimethyl dialkylammonium acetate copolymer, having the following general formula:

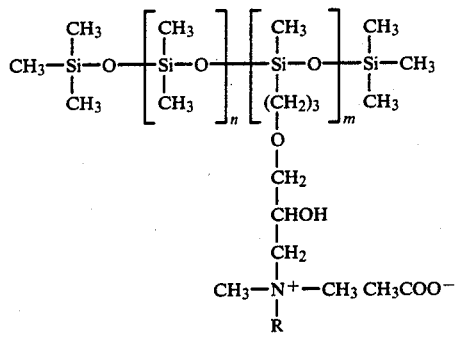

The betaine silicone compound is typified by polysiloxane polyalkyl betaine copolymer having the following general formula:

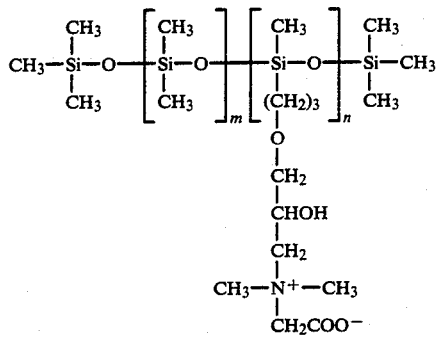

In constructing the applicator-wrap of the present invention, the preferred hair treatment composition incorporates other hair conditioning agents, in addition to QUATERNIUM-18 (dimethyl dihydrogenated tallow ammonium chloride) and dimethicone copolyol. Although an effective hair treatment composition can be made employing only these two compounds, it has been found that by including additional conditioning agents and, if desired, hair enhancing agents, the effectiveness of the applicator-wrap is greatly enhanced.

One of the additional hair conditioning agents incorporated in the preferred hair treatment composition is polyquaternium-6, which is a polymer of dimethyl diallylammonium chloride and has an empirical formula of $(C_8H_{16}N.Dl)_x$. The polyquaternium-6 or dimethyl diallylammonium chloride comprises a highly charged, cationic polymer which imparts lubricity, slip, and snarl-free wet combability to the hair. In addition, this compound is capable of adding a soft silky feel and anti-static properties to the hair, as well as imparting luster to dry hair. Furthermore, this polymer is capable of sealing and protecting split ends.

The final hair conditioning agent incorporated in the preferred composition of the hair treatment composition of the present invention is PEG 30 glyceryl cocoate. PEG 30 glyceryl cocoate is a water soluble form of the monoester of glycerin and coconut fatty acids. PEG 30 glyceryl cocoate is employed to impart added gloss, sheen and lubricity to the hair.

In addition to the hair conditioning agents detailed above, the preferred hair treatment composition of the present invention also incorporates several hair enhancing agents, which impart further improvements to the hair, once the treatment has been completed. These preferred hair enhancing agents comprise extracts from natural plants, flowers and herbs, as well as fragrance enhancers.

In the preferred embodiment, the hair enhancing agents incorporate sea kelp extract, neutral henna extract, chamomile extract and a fragrance enhancer. Preferably, the sea kelp extract comprises a 5-1 ratio mixture of sea kelp and glycerine.

Preferably, the henna extract comprises neutral henna. However, if color enhancing agents are desired, a specific color enhancing henna could be used, or a specific coloring agent can be employed with equal efficacy, without departing from the scope of this invention.

Finally, the preferred hair treatment composition of the present invention also incorporates preservatives and sequestering agents in order to assure that the end product has sufficient shelf life and the desired chemical interactions are attained.

In order to fully and completely detail the preferred hair treatment composition employed in the applicator-wrap of the present invention, Tables I and II are provided in which the effective amounts of each ingredient of the preferred hair treatment composition are fully and completely detailed. In Table I, the range of concentration for each ingredient of the hair treatment composition is provided, while Table II details the specific relative quantity of each constituent of the preferred formulation.

As is readily apparent from the preceding detailed disclosure, various compounds employed in the preferred composition can be eliminated, if desired. Consequently, Tables I and II must be considered as examples of the preferred composition, and should not be considered in any way to limit the scope of the present invention.

As detailed in Table II, the major ingredient employed in the hair treatment composition is deionized water. However, it must be remembered that the hair treatment composition, as exemplified in Tables I and II, is saturated into the fibrous carrier and then dried therein. Consequently, once the hair treatment composition has been fully and completely dried, the active chemicals retained in the applicator-wrap of this invention possess relative percentages which are increased by four to five times the amount shown in Tables I and II.

As a result, the hair treatment composition retained in the applicator-wrap and available for direct transfer and application to the hair fibers of the user is highly concentrated. In this way, the desirable, hair conditioning and enhancing effects previously sought but unattained are now attained by the applicator-wrap of this invention.

In alternate constructions, the hair treatment composition can be applied directly to the applicator-wrap with little or no water, to obtain the desired dry product. In addition, the hair treatment composition can be only partially dried from the applicator-wrap or not dried at all, thereby obtaining a wet hair conditioning and enhancing applicator-wrap. However, regardless of which process or alternate is used, the hair treatment composition should be adjusted to assure that the desired high concentration of hair conditioning and enhancing chemicals are retained in the applicator-wrap.

TABLE I

| PREFERRED HAIR TREATMENT COMPOSITION | % By Weight |
| --- | --- |
| Hair Conditioning Agents | |
| Quaternium-18 (dimethyl dihydrogenated tallow ammonium chloride) - 75% concentration | 5-60 |
| Dimethicone Copolyol | 1-15 |
| Polyquaternium-6 (dimethyldiallyammonium chloride) - 40% concentration | .1-10 |
| PEG 30 Glyceryl Cocoate | .75-10 |
| Hair Enhancing Agents | |
| Sea Kelp Extract | .001-5 |
| Neutral Henna Extract | .001-5 |
| Nettle Extract | .001-5 |
| Chamomile Extract | .001-5 |
| Fragrance | 0-5 |
| Preservatives and Sequestering Agents | |
| Disodium EDTA | .001-.5 |
| Methylparaben | .05-.75 |
| Imidazolidinyl Urea | .05-.5 |
| Deionized Water | Balance |

TABLE II

| PREFERRED HAIR TREATMENT COMPOSITION | % By Weight |
| --- | --- |
| Hair Conditioning Agents | |
| Quaternium-18 (dimethyl dihydrogenated tallow ammonium chloride) - 75% concentration | 18.5 |
| Dimethicone Copolyol | 4.0 |
| Polyquaternium-6 (dimethyldiallyammonium chloride) - 40% concentration | 1.5 |
| PEG 30 Glyceryl Cocoate | 1.5 |
| Hair Enhancing Agents | |
| Sea Kelp Extract | 0.01 |
| Neutral Henna Extract | 0.01 |
| Nettle Extract | 0.01 |
| Chamomile Extract | 0.01 |
| Fragrance | 0.50 |
| Preservatives and Sequestering Agents | |
| Disodium EDTA | 0.0025 |
| Methylparaben | 0.10 |
| Imidazolidinyl Urea | 0.10 |
| Deionized Water | 73.7575 |

Method of Manufacture

In order to attain the desired hair treatment applicator-wrap of the present invention, the desired hair conditioning and enhancing composition is produced and placed in a suitable container, which will accommodate the fibrous applicator-wrap and allow the hair treatment composition to be absorbed substantially throughout the fibrous material. Once the fibrous applicator-wrap has been submerged or dipped in the hair treatment composition for a sufficient length of time, the saturated applicator-wrap is removed and thoroughly dried, thereby eliminating substantially all of the water and attaining the desired concentrated level of each constituent of the hair treatment composition.

It has been found that after drying, the hair treatment applicator-wrap of the present invention must have at least twenty grams of hair treatment composition for each square meter of fibrous material. In addition, the amount of hair treatment composition retained in the applicator-wrap should not exceed thirty-five grams per square meter of material. Although an effective, useable, hair treatment applicator-wrap is attained with the hair treatment composition ranging between twenty grams and thirty-five grams of the hair treatment composition per square meter of flexible, fibrous material, the preferred range is between about twenty grams and twenty-six grams of hair treatment composition per square meter of flexible, fibrous material.

Using the teaching that has been provided, many alternate methods and processes can be employed to produce the hair treatment applicator-wrap of the present invention. However, two general processes have been found to be the most desirable and are detailed below.

Regardless of which method is employed, the initial step is the formulation of the hair treatment composition. The hair treatment composition is formulated by adding a sufficient quantity of deionized water into a stainless steel jacketed vessel which is equipped with a suitable mixer. The deionized water is then heated to about 45° C., or obtained at this temperature in an alternate manner.

When the proper temperature has been reached, the PEG 30 glyceryl cocoate and the dimethicone copolyol are stirred into the water. Once the temperature reaches 45° C. to 50° C., the methyl paraben is stirred into the solution.

The next steps preferably involve the addition of the quaternary compounds into the heated composition. In the preferred embodiment, the polyquaternium-6 or the dimethyl diallylammonium chloride is added to the solution and is stirred until completely dissolved. While this stirring is being carried out, the quaternium-18 or the dimethyl dihydrogenated tallow ammonium chloride is separately pre-melted by heating the hair conditioning agent to about 30° C. to 45° C. Once pre-melted, the quaternium-18 (dimethyl dihydrogrenated tallow ammonium chloride) is added to the mixture, and the entire mixture is stirred until homogeneous.

Once a substantially homogeneous mixture has been attained, all of the hair enhancing agents and preservatives are added to the mixture and stirred until the mixture is again homogeneous. As detailed above, these hair enhancing agents include the sea kelp/glycerin, neutral henna, and plant and herbal extracts, namely nettle extract and chamomile extract. In addition, the desired fragrance is also added to the composition along with disodium EDTA and imidazolidinyl urea. Finally, additional deionized water is added as is required to attain the desired relative amounts. Although this procedure is preferred and has been found to be efficient, no particular step or order of procedure is critical. Consequently, this process can be varied, without realizing any adverse results.

As an example of the quantity of each constituent employed in the preferred hair treatment composition, Table III has been provided. By referring to Table III, the precise quantity by weight or volume is detailed for each constituent in order to attain 100 gallons of the hair treatment composition.

TABLE III

| PREFERRED HAIR TREATMENT COMPOSITION | Amount |
| --- | --- |
| Deionized Water | 71.0 gals. |
| Quaternium-18 (dimethyl dihydrogenated tallow ammonium chloride) | 151.28 lbs. |
| Dimethicone Copolyol | 32.72 lbs. |
| Polyquaternium-6 | 12.26 lbs. |

TABLE III-continued

| PREFERRED HAIR TREATMENT COMPOSITION | Amount |
| --- | --- |
| (dimethyldiallyammonium chloride) | |
| PEG 30 Glyceryl Cocoate | 12.26 lbs. |
| Sea Kelp Extract | 0.082 lbs. |
| Neutral Henna Extract | 0.082 lbs. |
| Nettle Extract | 0.082 lbs. |
| Chamomile Extract | 0.082 lbs. |
| Fragrance | 1.85 kgs. |
| Disodium EDTA | 0.020 lbs. |
| Methylparaben | 0.818 lbs. |
| Imidazolidinyl Urea | 0.818 lbs. |
| Deionized Water | q.s. to 100 gals. |

Once a thorough homogeneous hair treatment composition has been attained, one of the two preferred processes is selected and followed. In the first process, the particular fibrous material is selected and saturated with the hair treatment composition by dipping or submerging the fibrous material into the hair treatment composition for a sufficient length of time to assure absorption of the hair treatment composition by the fibrous material. Then, the fibrous material is removed and dried.

In the preferred embodiment of the present invention, the fibrous material comprises a non-woven blend of rayon and polypropylene. In addition, this manufacturing process is preferably conducted as a continuous process, with a roll of rayon/polypropylene material being continuously drawn through a bath containing the aqueous hair treatment composition, while the composition is maintained between about room temperature and about 35° C.

Once the material has been drawn through the aqueous composition, the material is removed therefrom and passed to a drying zone where the water therein is driven off from the saturated material. Once fully and completely dried, the material is cut to the desired length and the desired hair treatment applicator-wrap of the present invention is obtained.

In the preferred embodiment, the drying process is achieved using heated rollers. However, many other well-known drying systems can be used, such as flow-through ovens, batch ovens or air blown dryers.

The second process which can be employed is generally referred to as a wet laid method. In this process, the homogenous, hair treatment composition is attained, substantially as detailed above. However, instead of saturating the fibrous material with the composition, the hair treatment composition is added to the fibers forming the applicator-wrap during the actual manufacturing of the applicator material.

By employing this method, the hair treatment composition is absorbed directly by the natural or synthetic fibers, just prior to the fibers being used to form the carrier substrate. Then, once the applicator substrate is attained, the substrate is dried and cut to the desired length. In this way, an efficient manufacturing process is realized.

If desired, many changes can be made to either of these processes such as using a batch system entirely, or cutting the material to the desired length prior to drying. Furthermore, the hair treatment composition could be sprayed onto the formed fibrous material or the fibers themselves, thereby eliminating the need for a chemical bath. Certainly, these variations, as well as other changes which would be apparent to one of ordinary skill in this art, will achieve substantially the same hair treatment applicator-wrap defined herein. Therefore, all of these variations and other obvious expedients are considered to be within the scope of the present invention.

Method of Use

As discussed above, the hair treatment applicator-wrap of the present invention is preferably constructed as a full head wrap in order to attain the optimum hair treatment and conditioning. In addition, it has been found that a specific method or process of using and applying the hair treatment applicator-wrap of the present invention should be followed to attain the most desirable results.

By employing the full head of hair applicator-wrap of the present invention and following the preferred application method, luxurious, healthy looking hair is attained which is fully moisturized and easily managed. Furthermore, the natural colors of the entire head of hair possess luster, gloss and sheen, while also having more body.

In the preferred application method, the hair is first shampooed and towel dried. If desired, a separate hair conditioner is applied and distributed evenly throughout the entire head of hair. Next, the hair treatment applicator-wrap of the present invention is applied completely around the entire head of hair and fastened with a clip, if necessary. Preferably, the hair wrapping is initiated in the front of the head and the rest of the hair wrapped therefrom, peripherally surrounding the entire head of hair.

Once the hair treatment applicator of the present invention has been fully and completely wrapped about the entire head of hair, a hot, damp salon towel is wrapped about the hair treatment applicator-wrap. This salon towel is left in position for about five to fifteen minutes.

Once the desired time interval has elapsed, the salon towel is removed and the hair treatment applicator-wrap is manipulated against the entire head of hair to completely distribute the hair conditioning agents and the hair enhancing agents throughout the entire head of hair, substantially to each and every hair fiber. Generally, this hair manipulation step should be performed for about three minutes. Once this hair manipulation step is completed, the hair is rinsed thoroughly and styled as desired.

It has been found that by employing the hair treatment applicator of the present invention, luxurious, healthy looking and moisturized hair is attained which is substantially more manageable, as well as possessing substantially enhanced luster, gloss and sheen. It has also been discovered that static fly-away is substantially eliminated and split ends are fully controlled. Furthermore, the hair exhibits added body and silkiness, without appearing heavy or weighted. As a result, the hair treatment applicator-wrap of the present invention provides a substantial advance over prior art systems, attaining results which have been previously unattainable.

Although variations can be made in the application process detailed above, without departing from the scope of the present invention, it has been found that the manipulation step, wherein the hair treatment applicator-wrap is manipulated throughout the head of hair to distribute the conditioner contained therein to each and every hair fiber, must be performed in order to attain the desired thorough hair enhancing and conditioning results with medium to long hair. However, with very short hair, the manipulation step may be unnecessary, since sufficient conditioning and enhancing agents are transferred to the hair fibers during the hot towel application.

EXAMPLE

In order to determine the effect of the applicator-wrap on a full head of hair at different concentration levels, several samples of the applicator-wrap were made. Each applicator-wrap comprised a blend of 80% rayon and 20% polypropylene, and measured 13 inches by 24 inches by 0.016 inches.

The hair treatment composiion was formulated in the manner detailed above and each sample was dipped into a bath containing the hair treatment composition. Prior to being placed in the bath, each sample was weighed. Once weighed, each sample was held in the bath for time intervals ranging between a few seconds to one minute. When removed from the bath, each sample was dried thoroughly, and then reweighed to determine the quantity of the hair treatment composition retained therein. The samples produced showed weight increases ranging between 4 grams and 6 grams. Since each applicator contains about 0.2 square meters, each of the applicator-wraps produced contained between 20 grams and 30 grams of hair treatment composition per square meter.

In order to test its effectiveness, a single applicator-wrap was then applied to the entire head of hair of different models whose hair lengths ranged from short to shoulder length. In each application, the method detailed above was followed.

In each application, a single applicator-wrap was found to provide the entire head of hair with substantially increased luster, sheen, gloss, manageability and a pleasant fragrance, as well as a silky and smooth feeling. None of the models found any area of their hair to be untreated.

It will thus be seen that the objects set forth above, among those made apparent from the preceding description, are efficiently attained and, since certain changes may be made in carrying out the above methods and in the articles set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described my invention, what we claim as new and desire to secure by Letters Patent is:

1. A hair conditioning and enhancing applicator system comprising
   A. a flexible carrier formed from fibrous material, and
   B. a hair treatment composition retained in the fibrous material for transferral to the hair fibers when desired, comprising
      a. at least one cationic hair conditioning agent,
      b. a water soluble or emulsifiable silicone-based compound, and
      c. a concentration of between about 20 and 30 grams for each square meter of fibrous material.

2. The hair conditioning and enhancing applicator system defined in claim 1, wherein said cationic hair conditioner is further defined as comprising a quaternium-18 or a dimethyl dihydrogenated tallow ammonium chloride and said silicone-based compound is further defined as comprising at least one selected from the group consisting of dimethicone copolyol, dimethicone, amodimethicone, stearoxytrimethylsilane, stearoxy dimethicone, polysiloxane polydimethyl dialkylammonium acetate copolymer and polysiloxane polyalkyl betaine copolymer.

3. The hair conditioning and enhancing applicator system defined in claim 2, wherein said hair treatment composition is further defined as comprising
   c. a polyquaternium-8 or a dimethyldiallyammonium chloride.

4. The hair conditioning and enhancing applicator system defined in claim 1, wherein said hair treatment composition is further defined as comprising
   c. hair enhancing agents comprising one or more selected from the group consisting of sea kelp extract, henna extract, chamomile extract, color enhancers, and fragrance enhancers.

5. The hair conditioning and enhancing applicator system defined in claim 1, wherein said hair treatment composition is further defined as being formed as an aqueous solution which is applied to the flexible, fibrous carrier as an aqueous composition, and subsequently dried, leaving the active chemicals retained therein.

6. The hair conditioning and enhancing applicator system defined in claim 1, wherein said fibrous material forming the flexible carrier is further defined as comprising one or more selected from the group consisting of rayons, nylons, polypropylenes, and polyesters, with said fibers or fibrous blends being woven or non-woven.

7. The hair conditioning and enhancing applicator system defined in claim 6, wherein said flexible carrier is further defined as comprising a size ranging between two inches by three inches to about sixteen inches by thirty-eight inches, and a thickness ranging between 0.001 inches and 0.050 inches.

8. The hair conditioning and enhancing applicator system defined in claim 6, wherein said flexible carrier is sized to allow the applicator to be quickly and easily wrapped about an entire head of hair and held in place with a single clip.

9. The hair conditioning and enhancing applicator system defined in claim 8, wherein said applicator wrap comprises a size of thirteen inches by twenty-four inches with a thickness of between about 0.016 and 0.017 inches.

10. A hair conditioning and enhancing applicator system comprising
    A. a flexible carrier formed from fibrous material selected from one or more of the group consisting of rayon, nylon, polypropylene and polyester, and formed in a size and shape for convenient application to a head of hair, and
    B. a hair treatment composition retained in said fibrous material for transferral to the hair fibers when applied thereto, said composition comprising
       a. between about five and sixty percent by weight of quaternium-18 (dimethyl dihydrogenated tallow ammonium chloride),
       b. between about one and fifteen percent by weight of dimethicone copolyol, c. between about 0.1 and 10 percent by weight of polyquaternium-6 (dimethyldiallyammonium chloride),
d. between about 0.75 and 10 percent by weight of a PEG 30 glyceryl cocoate, and
e. the balance thereof comprising one or more selected from the group consisting of hair enhancing agents, preservatives, and sequestering agents.

11. The hair conditioning and enhancing applicator system defined in claim 10, wherein said hair treatment composition contained in the fibrous material is further defined as comprising
f. between about 0.001 and 5 percent by weight of sea kelp extact,
g. between about 0.001 and 5 percent by weight of henna extract,
h. between about 0.001 and 5 percent by weight of nettle extract,
i. between about 0.001 and 5 percent by weight of chamomile extract, and
j. between about 0 and 5 percent of a fragrance enhancer.

12. The hair conditioning and enhancing applicator system defined in claim 11, wherein said hair treatment composition is further defined as comprising
k. between about 0.001 and 0.5 percent by weight of disodium EDTA,
l. between about 0.5 and 0.75 percent by weight of methylparaben, and
m. between about 0.5 and 0.75 percent by weight of imidazolidinyl urea.

13. A hair conditioning and enhancing applicator system comprising
A. a flexible carrier formed from fibrous material selected from one or more of the group consisting of rayon, nylon, polypropylene and polyester, and formed in a size and shape for convenient application to a head of hair, and
B. a hair treatment composition retained in said fibrous material for transferral to the hair fibers when applied thereto, said composition comprising
a. about seventy percent by weight of quaternium-18 (dimethyl dihydrogenated tallow ammonium chloride),
b. about fifteen percent by weight of dimethicone copolyol,
c. about 6 percent by weight of polyquaternium-6 (dimethyldiallyammonium chloride),
d. about 6 percent by weight of PEG 30 glyceryl cocoate, and
e. the balance thereof comprising one or more selected from the group consisting of hair enhancing agents, preservatives, and sequestering agents.

14. The hair conditioning and enhancing applicator system defined in claim 13, wherein said hair treatment composition contained in the fibrous material is further defined as comprising
f. about 0.04 percent by weight of sea kelp extact,
g. about 0.04 percent by weight of henna extract,
h. about 0.04 percent by weight of nettle extract,
i. about 0.04 percent by weight of chamomile extract, and
j. about 2 percent by weight of a fragrance enhancer.

15. The hair conditioning and enhancing applicator system defined in claim 14, wherein said hair treatment composition is further defined as comprising
k. about 0.01 percent by weight of disodium EDTA,
l. about 0.4 percent by weight of methylparaben, and
m. about 0.4 percent by weight of imidazolidinyl urea.

16. A method for conditioning and enhancing an entire head of hair comprising the steps of
A. obtaining an applicator comprising
a. a flexible carrier formed from fibrous material, and
b. a hair treatment composition retained in the fibrous material for transferral to the hair fibers, comprising
1. at least one cationic hair conditioning agent,
2. a water soluble or emulsifiable silicone-based compound, and
3. a concentration of between about 20 and 30 grams for each square meter of fibrous material;
B. shampooing the hair to be treated;
C. drying the hair;
D. wrapping the applicator about the entire head of hair;
E. applying a hot, damp towel over the wrapped applicator;
F. waiting about five to fifteen minutes;
G. removing the damp towel; and
H. rubbing the applicator throughout the hair as required for added transfer;
I. rinsing the hair thoroughly; and
J. styling the hair as desired.

* * * * *